(12) United States Patent
Geist

(10) Patent No.: US 10,058,350 B2
(45) Date of Patent: Aug. 28, 2018

(54) ACCESS ASSEMBLY FOR ANTERIOR AND LATERAL SPINAL PROCEDURES

(71) Applicant: Integrity Implants, Inc., Cooper City, FL (US)

(72) Inventor: Wyatt Drake Geist, Davie, FL (US)

(73) Assignee: Integrity Implants, Inc., Cooper City, FL (US)

( * ) Notice: Subject to any disclaimer, the term of this patent is extended or adjusted under 35 U.S.C. 154(b) by 0 days.

(21) Appl. No.: 15/274,723

(22) Filed: Sep. 23, 2016

(65) Prior Publication Data

US 2017/0086878 A1     Mar. 30, 2017

Related U.S. Application Data

(60) Provisional application No. 62/232,021, filed on Sep. 24, 2015.

(51) Int. Cl.
| | |
|---|---|
| *A61B 17/02* | (2006.01) |
| *A61B 17/34* | (2006.01) |
| *A61B 5/00* | (2006.01) |
| *A61B 90/57* | (2016.01) |
| *A61M 29/00* | (2006.01) |

(52) U.S. Cl.
CPC ........ *A61B 17/3403* (2013.01); *A61B 5/4893* (2013.01); *A61B 17/0218* (2013.01); *A61B 17/3423* (2013.01); *A61B 90/57* (2016.02); *A61M 29/00* (2013.01); *A61B 2017/0262* (2013.01); *A61B 2017/3407* (2013.01)

(58) Field of Classification Search
CPC ............ A61B 17/3403; A61B 17/0218; A61B 7/3423; A61B 90/57; A61B 5/4893; A61B 2017/0262; A61B 2017/3407; A61M 29/00

USPC .......... 606/246–279, 86 R; 623/17.11–17.16; 600/201–214; 128/898
See application file for complete search history.

(56) References Cited

U.S. PATENT DOCUMENTS

| | | | |
|---|---|---|---|
| 3,750,667 | A | 8/1973 | Pshenichny et al. |
| 4,580,563 | A | 4/1986 | Gross |
| 5,013,318 | A | 5/1991 | Spranza, III |
| 5,484,437 | A | 1/1996 | Michelson |

(Continued)

FOREIGN PATENT DOCUMENTS

WO     WO0217206     2/2002

OTHER PUBLICATIONS

Unger and Kowitt, "Flight back—iPhone application to fight florida traffic ticket.", Internet article: http://udm4.com/Phone/Fight_Back_Florida_T-3957004, (retrieved Mar. 18, 2013).

(Continued)

*Primary Examiner* — Pedro Philogene
(74) *Attorney, Agent, or Firm* — McHale & Slavin, P.A.

(57) ABSTRACT

The present invention is directed to methods and instrumentation for performing surgery on the spine along its lateral aspect (side) and generally by a lateral, anterior or an anterolateral surgical approach, such that the instruments enter the body from an approach that is other than posterior and make contact with the spine along its lateral aspect. The present invention provides for the entire surgical procedure to be performed through a relatively small incision and may be performed in either the thoracic or lumbar spine.

12 Claims, 10 Drawing Sheets

(56) References Cited

U.S. PATENT DOCUMENTS

| | | | |
|---|---|---|---|
| 5,741,253 A | 4/1998 | Michelson | |
| 6,063,088 A | 5/2000 | Winslow | |
| 6,228,022 B1 | 5/2001 | Friesem et al. | |
| 6,283,966 B1 | 9/2001 | Houfburg | |
| 6,506,151 B2 | 1/2003 | Estes et al. | |
| 6,589,247 B2 | 7/2003 | McGahan et al. | |
| 6,740,091 B2 | 5/2004 | Kohrs et al. | |
| 6,770,074 B2 | 8/2004 | Michelson | |
| 6,916,323 B2 | 7/2005 | Kitchens et al. | |
| 7,083,623 B2 | 8/2006 | Michelson | |
| 7,207,991 B2 | 4/2007 | Michelson | |
| 7,244,258 B2 | 7/2007 | Burkus et al. | |
| 7,326,214 B2 | 2/2008 | Michelson | |
| 7,431,722 B1 | 10/2008 | Michelson | |
| 7,491,205 B1 | 2/2009 | Michelson | |
| 7,569,054 B2 | 8/2009 | Michelson | |
| 7,597,695 B2 | 10/2009 | Schmiel et al. | |
| 7,686,805 B2 | 3/2010 | Michelson | |
| 7,686,807 B2 | 3/2010 | Padget et al. | |
| 7,717,917 B2 | 5/2010 | Kofoed | |
| 7,722,619 B2 | 5/2010 | Michelson | |
| 7,771,475 B2 | 8/2010 | Michelson | |
| 7,905,884 B2 | 3/2011 | Simonton et al. | |
| 7,909,832 B2 | 3/2011 | Michelson | |
| 7,914,530 B2 | 3/2011 | Michelson | |
| 7,918,855 B2 | 4/2011 | Michelson | |
| 7,955,360 B2 | 6/2011 | Michelson | |
| 7,972,365 B2 | 7/2011 | Michelson | |
| 7,992,729 B1 | 8/2011 | Labonia, Jr. et al. | |
| 7,993,347 B1 | 8/2011 | Michelson | |
| 7,998,143 B2 | 8/2011 | Michelson | |
| 8,066,709 B2 | 11/2011 | Michelson | |
| 8,066,710 B2 | 11/2011 | Estes et al. | |
| 8,328,716 B2 | 12/2012 | Schmieding et al. | |
| 8,343,189 B2 | 1/2013 | Assell et al. | |
| 8,372,076 B2 | 2/2013 | Simonton et al. | |
| 8,403,841 B2 | 3/2013 | Miles et al. | |
| 8,449,463 B2 | 5/2013 | Nunley et al. | |
| 8,480,676 B2 | 7/2013 | Lyon | |
| 8,496,709 B2* | 7/2013 | Schell | A61B 17/7064 606/99 |
| 8,518,087 B2* | 8/2013 | Lopez | A61B 18/1487 606/279 |
| 8,535,322 B1 | 9/2013 | Powlan | |
| 8,617,167 B2 | 12/2013 | Weisel et al. | |
| 8,641,719 B2 | 2/2014 | Gephart et al. | |
| 8,721,536 B2 | 5/2014 | Marino et al. | |
| 8,753,345 B2 | 6/2014 | McCormack et al. | |
| 8,795,167 B2 | 8/2014 | Ainsworth et al. | |
| 8,852,243 B2* | 10/2014 | Morgenstern Lopez | A61B 18/1487 606/279 |
| 9,463,052 B2 | 10/2016 | Geist | |
| 2002/0032447 A1* | 3/2002 | Weikel | A61B 17/1671 606/86 R |
| 2002/0077641 A1 | 6/2002 | Michelson | |
| 2003/0032865 A1 | 2/2003 | Estes et al. | |
| 2003/0233094 A1 | 12/2003 | Squires et al. | |
| 2004/0024408 A1 | 2/2004 | Burkus et al. | |
| 2004/0068264 A1 | 4/2004 | Treace | |
| 2005/0143825 A1 | 6/2005 | Enayati | |
| 2005/0261681 A9 | 11/2005 | Branch | |
| 2005/0261684 A1 | 11/2005 | Shaolian et al. | |
| 2006/0084992 A1 | 4/2006 | Michelson | |
| 2006/0200238 A1 | 9/2006 | Schmiel et al. | |
| 2007/0055379 A1 | 3/2007 | Stone et al. | |
| 2007/0233252 A1 | 10/2007 | Kim | |
| 2007/0270875 A1 | 11/2007 | Bacher et al. | |
| 2008/0071279 A1 | 3/2008 | Bandeira et al. | |
| 2008/0108875 A1 | 5/2008 | Kunkel et al. | |
| 2008/0140013 A1 | 6/2008 | Kunkel et al. | |
| 2008/0255667 A1 | 10/2008 | Horton et al. | |
| 2009/0125030 A1 | 5/2009 | Tebbe et al. | |
| 2009/0131986 A1 | 5/2009 | Lee et al. | |
| 2009/0138053 A1 | 5/2009 | Assell et al. | |
| 2009/0143863 A1 | 6/2009 | Perez-Cruet | |
| 2009/0164020 A1 | 6/2009 | Janowski et al. | |
| 2009/0171389 A1 | 7/2009 | Sankaran | |
| 2009/0216238 A1 | 8/2009 | Stark | |
| 2009/0265007 A1 | 10/2009 | Colleran | |
| 2009/0306671 A1 | 12/2009 | McCormack et al. | |
| 2010/0160984 A1 | 6/2010 | Berry et al. | |
| 2010/0174147 A1 | 7/2010 | Miles et al. | |
| 2010/0174148 A1 | 7/2010 | Miles et al. | |
| 2010/0191241 A1 | 7/2010 | McCormack et al. | |
| 2010/0191296 A1 | 7/2010 | Lyon | |
| 2010/0198226 A1 | 8/2010 | Estes et al. | |
| 2010/0217088 A1 | 8/2010 | Heiges et al. | |
| 2010/0241124 A1 | 9/2010 | Housman et al. | |
| 2010/0331845 A1 | 12/2010 | Foley et al. | |
| 2011/0028791 A1 | 2/2011 | Marino et al. | |
| 2011/0032078 A1 | 2/2011 | Guziel et al. | |
| 2011/0040154 A1 | 2/2011 | Reznik | |
| 2011/0054537 A1 | 3/2011 | Miller et al. | |
| 2011/0106186 A1 | 5/2011 | Wolfson | |
| 2011/0152866 A1 | 6/2011 | Knutson | |
| 2011/0196494 A1 | 8/2011 | Yedlicka et al. | |
| 2011/0213432 A1 | 9/2011 | Geist et al. | |
| 2011/0224742 A1 | 9/2011 | Weisel et al. | |
| 2011/0238184 A1 | 9/2011 | Zdeblick et al. | |
| 2011/0251461 A1 | 10/2011 | Gomez Gonzalez et al. | |
| 2012/0071984 A1 | 3/2012 | Michelson | |
| 2012/0172670 A1 | 7/2012 | Hamada | |
| 2012/0203071 A1 | 8/2012 | Osman | |
| 2012/0232552 A1 | 9/2012 | Morgenstern Lopez et al. | |
| 2012/0232658 A1 | 9/2012 | Morgenstern Lopez et al. | |
| 2012/0296171 A1 | 11/2012 | Lovell et al. | |
| 2012/0323331 A1 | 12/2012 | Michelson | |
| 2013/0006364 A1 | 1/2013 | McCormack et al. | |
| 2013/0013000 A1 | 1/2013 | Ainsworth et al. | |
| 2013/0013070 A1 | 1/2013 | McCormack et al. | |
| 2013/0018474 A1 | 1/2013 | McCormack et al. | |
| 2013/0023995 A1 | 1/2013 | McCormack et al. | |
| 2013/0023996 A1 | 1/2013 | McCormack et al. | |
| 2013/0030532 A1 | 1/2013 | McCormack et al. | |
| 2013/0103103 A1 | 4/2013 | Mire et al. | |
| 2013/0150678 A1 | 6/2013 | Miles et al. | |
| 2013/0184771 A1 | 7/2013 | Geist | |
| 2013/0190769 A1 | 7/2013 | Morgenstern Lopez et al. | |
| 2013/0310943 A1 | 11/2013 | McCormack et al. | |
| 2013/0338674 A1 | 12/2013 | Geist et al. | |
| 2013/0345667 A1 | 12/2013 | Lyon | |
| 2013/0345712 A1 | 12/2013 | Geist et al. | |
| 2014/0031874 A1 | 1/2014 | Kucharzyk et al. | |
| 2014/0067069 A1 | 3/2014 | Lopez | |
| 2014/0074170 A1 | 3/2014 | Mertens et al. | |
| 2014/0014360 A1 | 4/2014 | Gephart et al. | |
| 2014/0100657 A1 | 4/2014 | McCormack et al. | |
| 2014/0100660 A1 | 4/2014 | Morgenstern Lopez et al. | |
| 2014/0121467 A1 | 5/2014 | Vayser et al. | |
| 2014/0180418 A1 | 6/2014 | Janowski et al. | |
| 2014/0214165 A1 | 7/2014 | Schell et al. | |
| 2017/0071588 A1* | 3/2017 | Choi | A61B 17/0293 |

OTHER PUBLICATIONS

Hanna, A., "The Alex Hanna mobile app", Internet article: http://www.appszoom.com/iphone-apps/reference/alex-hanna-pa_evltp.html, (retrieved Mar. 18, 2013).

Bensen & Bingham, "24 Hour ticket power traffic ticket attorney", Las Vegas, Nevada, Internet Article: http://24hourticketpower.com, (retrieved Mar. 18, 2013).

Ziu, I., "Parking ticket pundit NYC iPhone", Internet article: http://www.appszoom.com/iphone-apps/utilities/parking-ticket-pundit-nyc_d1htb.html, (retrieved Mar. 19, 2013).

Anonymous, "No traffic tickets. How to get out of a traffic ticket! 2.1.7 App for iPad, iPhone . . . ", Internet article: http://appfinder.lisisoft.com/app/no-traffic-tickets-how-to.html, (retrieved Mar. 18, 2013).

Anonymous, "Backseat lawyer", Internet article: http://udm4.com/iPhone/Backseat_Lawyer-3621608, (retrieved Mar. 18, 2013).

(56) References Cited

OTHER PUBLICATIONS

Bharath, M., "Fight your ticket 1.1 App for iPad, iPhone, Medical", Internet article: http://appfinder.lisisoft.com/app/fight-your-ticket.html, (retrieved Mar. 18, 2013).
Anonymous, "Pocket attorney app. a lawyer in your pocket", Internet article: http://pocketattorneyapp.com, (retrieved Mar. 18, 2013).
Rand, "Babkes law iPhone", Internet article: http://www.appszoom.com/iphone-apps/business/babkes-law_eumjc.html, (retrieved Mar. 19, 2013).
Ticketdefender LLC, "TicketDefender iPhone", Internet article: http://www.appszoom.com/iphone-apps/navigation/ticketdefender_efjcs.html, (retrieved Mar. 18, 2013).
Anonymous, "Don't pay that speeding ticket. How to fight a traffic ticket or moving radar violation", Internet article: http://www.appszoom.com/iphone-apps/lifestyle/dont-pay-that-speeding-ticket-how-to-fight-a-traffic-ticket-or-moving-radar-violation-in-court-a_dvcmp.html?nav=related. (retrieved Mar. 18, 2013).
Nextgenmobile, "File my tickets—Android", Internet article: http://pt.appszoom.com/android_applications/transportation/file-my-tickets_cbhwe.html, (retrieved Mar. 18, 2013).
JDG, "Fight that ticket—SlideMe v.2.8", Internet article: http://slideme.org/application/fight-ticket, (retrieved Mar. 18, 2013).
Ticketbust.com, "iTicketBust for iPhone, iPod touch, and iPad on the iTunes app store", Internet article: https://itunes.apple.com/app/iticketbust/id425364397, (retrieved Mar. 18, 2013).
Anonymous, "Mr. Ticket traffic attorney mobile app", Internet article: http://www.mrtickettrafficattorney.com/mrticketmobileapp, (retrieved Mar. 18, 2013).
Anonymous, "TicketVoid fight your ticket", Internet article: http://appfinder.lisisoft.com/app/ticket-void-traffic-ticket.html, (retrieved Mar. 18, 2013).

* cited by examiner

ACCESS ASSEMBLY FOR ANTERIOR AND LATERAL SPINAL PROCEDURES

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 62/232,021, entitled "ACCESS ASSEMBLY FOR ANTERIOR AND LATERAL SPINAL PROCEDURES", filed Sep. 24, 2015. The contents of which the above referenced application is incorporated herein by reference.

FIELD OF INVENTION

The present invention relates generally to stabilization of adjacent bony structures of the spine; and more particularly, to an assembly and method for providing anterior and/or lateral access to the disc space of the vertebrae for providing stabilization to the bony structures thereof.

BACKGROUND INFORMATION

It is widely held that healing and/or structural correction is greatly facilitated when a bone is stabilized in the proper position. Various devices for stabilization of bone are well known and routinely practiced in the medical arts. For example, an abnormal spine can be stabilized using a substantially rigid or semi-rigid interconnecting means (rod or plate) and fastening means (screws, clamps, hooks, claws, anchors, or bolts). Multiple fasteners are placed into the spinal pedicle of each vertebra and linked by at least one interconnecting means. Once in place, these systems substantially immobilize the spine and promote bony fusion (arthrodesis).

With respect to the thoracic spine, it may be afflicted with a variety of ailments, some so severe as to require surgical intervention. A disc herniation may compress the spinal cord and/or nerve roots and cause pain, loss of function, and even complete paralysis of the legs with loss of bowel and bladder control. The correct treatment for such conditions is the removal of the offending discal tissue. However, this has proven both difficult and quite dangerous. When the discs of the thoracic spine are approached posteriorly (from behind), the spinal cord is in the way. To approach the same herniation anteriorly (from the front) requires the very formidable procedure of thoracotomy (cutting open the chest) and moving the heart and lungs out of the way.

Quite recently, surgeons have begun performing these procedures from a lateral approach to the spine (from the side) using fiber optic viewing instruments called thorascopes and numerous small surgical openings through the chest wall (portals) through which various surgical instruments, such as burrs, rongeurs and curettes, may be placed to remove these disc herniations while avoiding formal thoracotomy. Because the discs are very narrow in the thoracic spine and the surgeon is approaching the spine laterally, there is very little space in which to work as the disc is entered. Therefore, the amount of disc removal may be limited. Alternatively, the surgeon might remove the pedicle to gain access to the spinal canal, risking further weakening of the already diseased area.

For a variety of reasons, including the removal of disc material, the thoracic spine may sometimes become unstable (too much motion) at any given level. Historically, this has been treated by fusion, the joining together permanently of the unstable vertebrae via a bridge of bone so as to eliminate all motion at that location. Fusions about the thoracic spine have been performed either anteriorly or posteriorly, either procedure being a serious surgical undertaking.

Stability of the spine is required for fusion to Occur. For this reason, and for the purpose of correcting spinal deformity, it is often necessary to use hardware to rigidly internally fixate (stabilize) the spine. To date, the only benefit the use of the thorascope has provided in this regard is to allow the previous thoracotomy incision to be somewhat smaller.

Thus, the prior art includes numerous drawbacks which have not been entirely addressed. Traditionally, the surgical techniques for stabilization of bone required large incisions (upwards of 6 cm in length) and a considerable amount of muscle be cut and stripped away (retracted) from the bone for an "open" visualization of the bone and access thereto for the placement of the fasteners and instrument implantation. Although this so-called "open" surgical technique has successfully treated non-unions, instability, injuries and disease of the spine, it is not without disadvantages. Given the invasive nature of this technique, a lengthy healing time and considerable post-operative pain for the patient is common.

With respect to the human lumbar spine, the treatment of discal disease with neural compression has generally been from a posterior (from behind) approach. Lumbar discs are generally quite large, and it is only those protrusions occurring posteriorly which compress the neural elements, which are themselves posterior to the discs. These posterior approaches have included both true posterior approaches and posterolateral approaches to the discs. Further, such approaches have been made via open incisions or through percutaneous stab wounds. In the latter case, instruments are inserted through the stab wounds and monitored by the use of radiographic imaging or the use of an endoscopic viewing device. While it is possible to also decompress a posterior disc herniation in the lumbar spine from an anterior approach (from the front), doing so requires the removal of a very substantial portion or all of the disc material in the front and mid portions of the disc, thus leaving that disc and that spinal segment generally unstable. Therefore, such an anterior approach to the lumbar spine has been reserved for those instances where a fusion is to be performed in conjunction with, and following such a disc removal.

Fusion is generally induced with the application of bone or bone like substances between bones to induce bony bridging; such procedures have been performed outside the vertebral bodies and/or between the vertebral bodies, the latter being known as an interbody fusion. Such interbody fusions have been performed from posterior, posterolateral and anterior. Interbody fusion from the posterior approach, while still in use, has been associated with significant complications generally related to the fact that the delicate dural sac and the spine nerves cover the back of the disc space and are, thus, clearly at risk for damage with such an approach. The posterolateral approach has generally been utilized as a compliment to percutaneous discectomy and has consisted of pushing tiny fragments of morselized bone down through a tube and into the disc space.

In anterior interbody spinal fusion, the path of entry of the fusion material into the intervertebral space is performed from a straight anterior position. Such an anterior position is achieved in one of two ways. First, by a straight anterior approach which requires that the peritoneal cavity, which contains the intestines and other organs, be punctured twice, once through the front and once through the back on the way to the front of the spine; or secondly, by starting on the front of the abdomen off to one side and dissecting behind the peritoneal cavity on the way to the front of the spine. Regardless of which approach to the front of the spine is used, and apart from the obvious dangers related to the dense anatomy and vital structures in that area, there are at least two major problems specific to the anterior interbody fusion angle of implant insertion itself. First, generally at the L.sub.4 and L.sub.5 discs, the great iliac vessels bifurcate from the inferior vena cava and lie in close apposition to and covering that disc space, making fusion from the front both difficult and dangerous. Secondly, anterior fusions have generally been done by filling the disc space with bone or by drilling across the disc space and then filling those holes with shaped implants. As presently practiced, the preferred method of filling the disc space consists of placing a ring of allograft (bone not from the patient) femur into that disc space. An attempt to get good fill of the disc space places the sympathetic nerves along the sides of the disc at great risk. Alternatively, when the dowel technique is used, because of the short path from the front of the vertebrae to the back and because of the height of the disc as compared to the width of the spine, only a portion of the cylindrical implant or implants actually engage the vertebrae; thus compromising the support provided to the vertebrae and the area of contact provided for the fusion to occur.

There is, therefore, in regard to the lumbar spine, a need for a new method and apparatus for achieving interbody fusion which avoids the problems associated with all prior methods, and which have included, but are not limited to, nerve damage when performed posteriorly, or the need to mobilize the great iliac vessels when performed anteriorly. Further, the size of the implants is limited by the dural sac posteriorly, and the width of the spine and the delicate vital structures therewith associated anteriorly. Such a method and apparatus for interbody fusion should provide for optimal fill of the interspace without endangering the associated structures, and allow for the optimal area of contact between the implant or implants and the vertebrae to be fused. The method and apparatus should also provide controlled distraction of the bony structures, while also providing ease of access to the damaged area of the spine while minimizing risk to the patient.

SUMMARY OF THE INVENTION

Briefly, the present invention is directed to methods and instrumentation for performing surgery on the spine along its lateral aspect (side), and generally by a lateral, anterior or an anterolateral surgical approach, such that the instruments enter the body from an approach that is other than posterior and make contact with the spine along its lateral aspect. The present invention provides for the entire surgical procedure to be performed through a relatively small incision or puncture which may be performed in either the thoracic or lumbar spine.

In the preferred embodiment, the access assembly of the present invention comprises a needle assemble including an elongated handle, the needle assembly having a removable needle member for insertion of a guide wire and a first stage dilator that forms an outer surface of the needle cannula. In at least one embodiment, the first stage dilator feature of the needle assembly may also be utilized for providing additional controlled dilation of the tissue by acting as a guide for additional stages of dilators. A guide wire may be provided for insertion into the disc space through the lumen of the needle assembly with the assistance of x-rays, thorascope, image intensifier, direct vision or the like. For example, for surgery in the thoracic spine, a small incision in the chest cavity of the patient is made from a lateral approach to the thoracic spine. For surgery in the lumbar spine, a small incision may be made in the abdominal wall of the patient. Once positioned, the guide wire extends between the disc space to outside of the patient to provide a guideway for surgical tools and implants. The needle assembly includes an inner needle member and a cannula which are secured together with the elongated handle member through a split shoulder connection which allows an anvil area on the distal end of the needle member suitable for striking with a mallet or the like. The elongated handle includes a U-notch and a rotatable portion for retaining the needle and the cannula in an assembled arrangement. The first stage dilator includes an inner bore sized for cooperation with the outer surface of the cannula member and is preferably integrally formed thereto. The second stage dilator includes an inner bore sized to cooperate with the outer surface of the first stage dilator. In some embodiments, third and fourth stage dilators may be provided. In this manner, each successive dilator acts as a guideway for the next larger dilator.

Once the largest desired dilator tube is in place within the patient, the cannula and guide wire may be removed, providing an access tunnel to the disc space. The inner diameter of the outer dilator, e.g. tunnel, is provided with sufficient diameter for disc modification or removal, as well as the placement of spacers, bone fragments, implants and the like to be passed therethrough to the disc space. In at least one embodiment, the components of the system are constructed to either be constructed from electrically conductive materials or include electrically conductive pathways for use with neurophysiological monitoring equipment. Once the operation is completed, rotation and/or pulling on the dilator releases the dilator tube for removal from the patient.

Accordingly, it is an objective of the present invention to provide a device and method for performing surgery on the thoracic spine through the chest cavity from a lateral approach to the spine.

It is a further objective of the present invention to provide a device and method for performing a thoracic discectomy, an interbody fusion, and rigid internal fixation of the spine through the chest cavity from a lateral approach as a single integrated procedure.

It is yet a further objective of the present invention to provide a device and method for performing a lumbar fusion from the lateral aspect of the spine.

It is another objective of the present invention to provide a method and device for performing a lumbar fusion and spinal canal decompression from the lateral aspect of the spine.

It is yet another objective of the present invention to provide a device and method for performing a lumbar fusion, decompressive discectomy, and a rigid internal fixation of the spine as a single integrated surgical procedure.

It is still yet another objective of the present invention to provide a device and method to achieve discectomy, fusion and interbody stabilization of the lumbar without the need to mobilize the great iliac vessels from the front of the vertebral bodies.

It is still yet another objective of the present invention to provide a device for performing surgery on the spine that includes a needle assembly having a removable handle for locating the proper position related to the bony structure, whereby the handle may be removed for dilation of the entry path providing a tunnel to the surgical site.

It is still yet another objective of the present invention to provide a device for performing surgery on the spine that includes an integrally formed first stage dilator formed onto the outer surface of a needle cannula.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENTS

Figure 1:
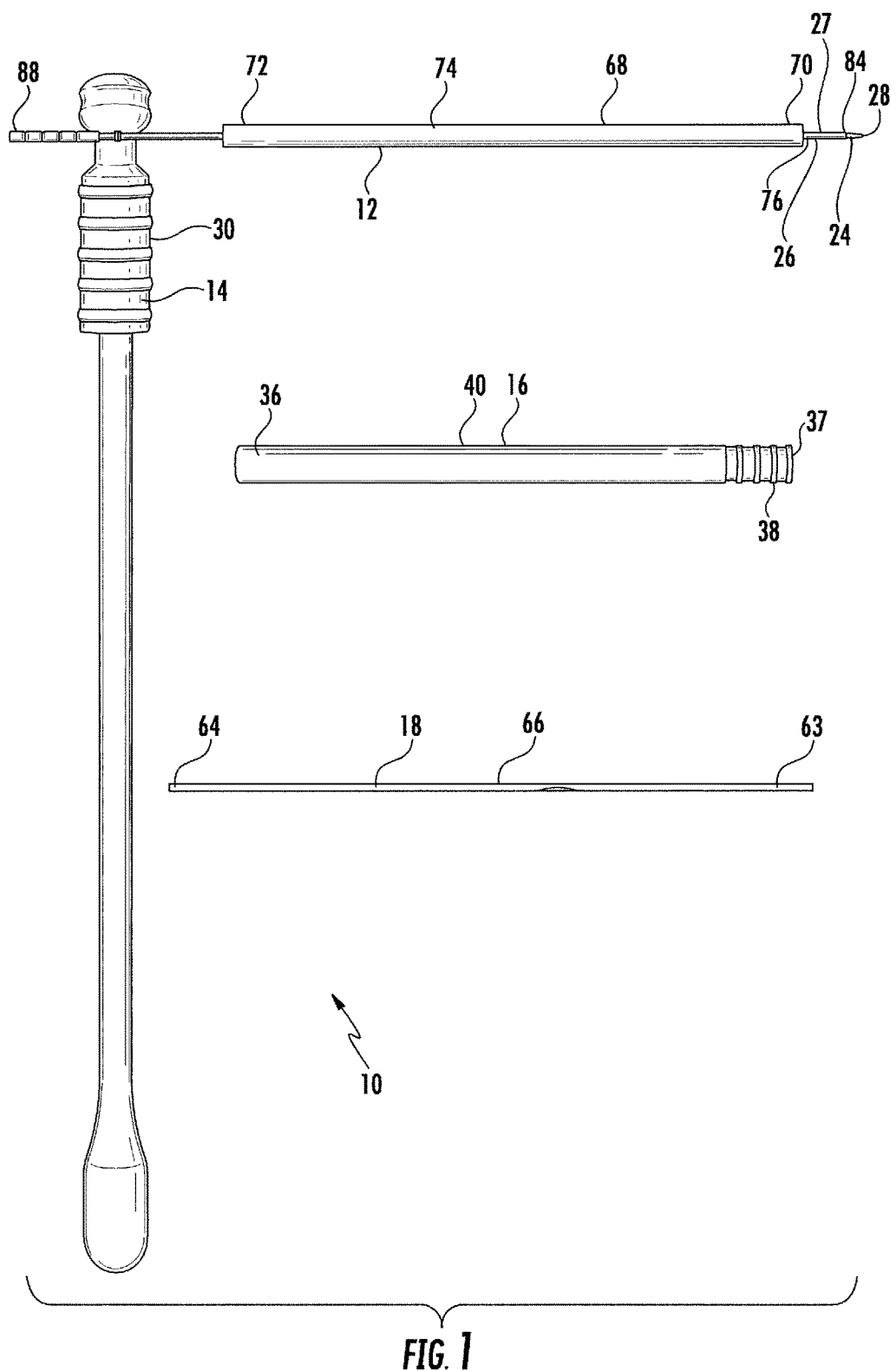
FIG. 1 is a plan view illustrating one embodiment of the present invention.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Figure 2:
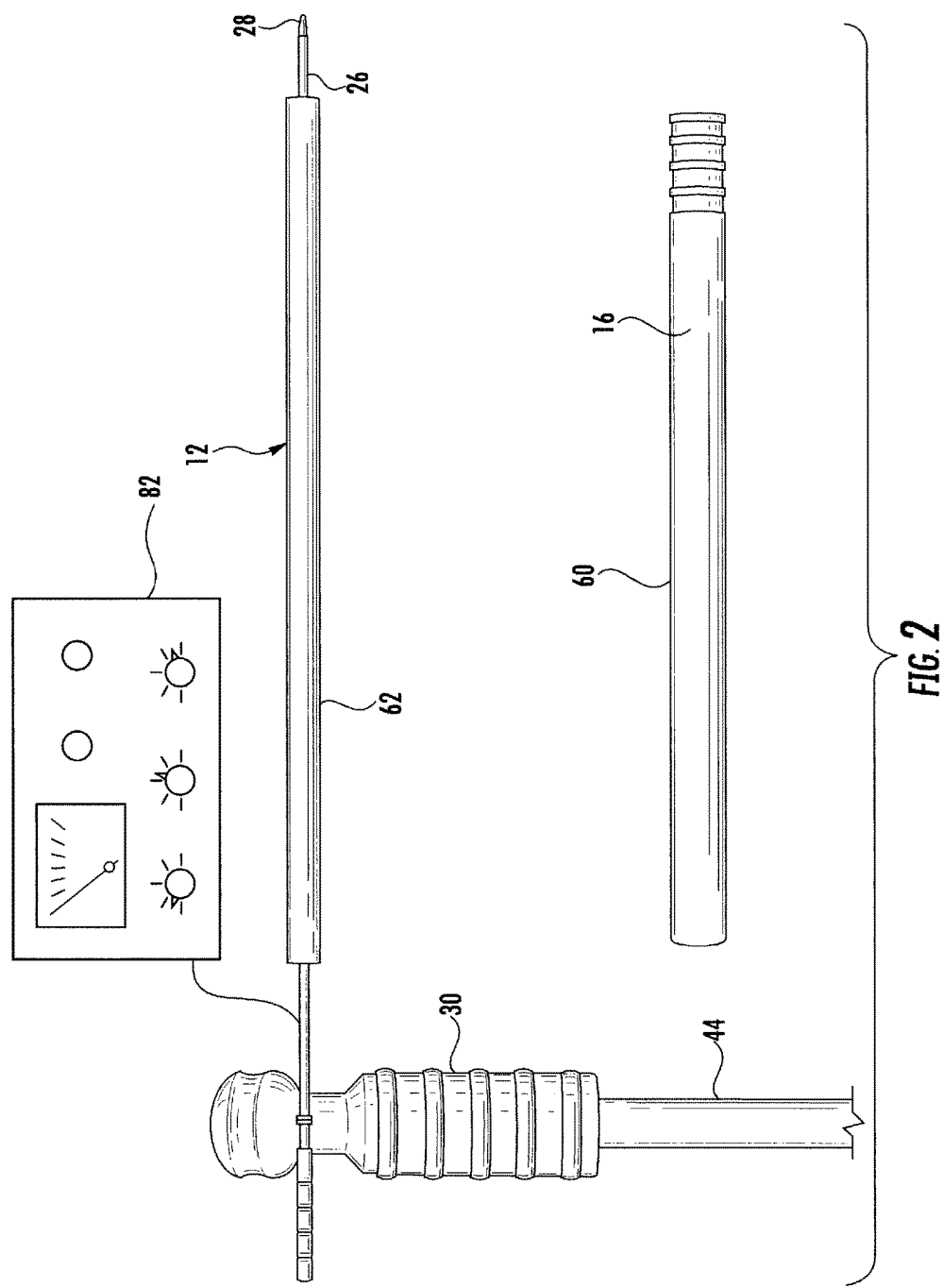
FIG. 2 is a partial plan view of the embodiment shown in FIG. 1 illustrating the first end thereof.
Figure 3:
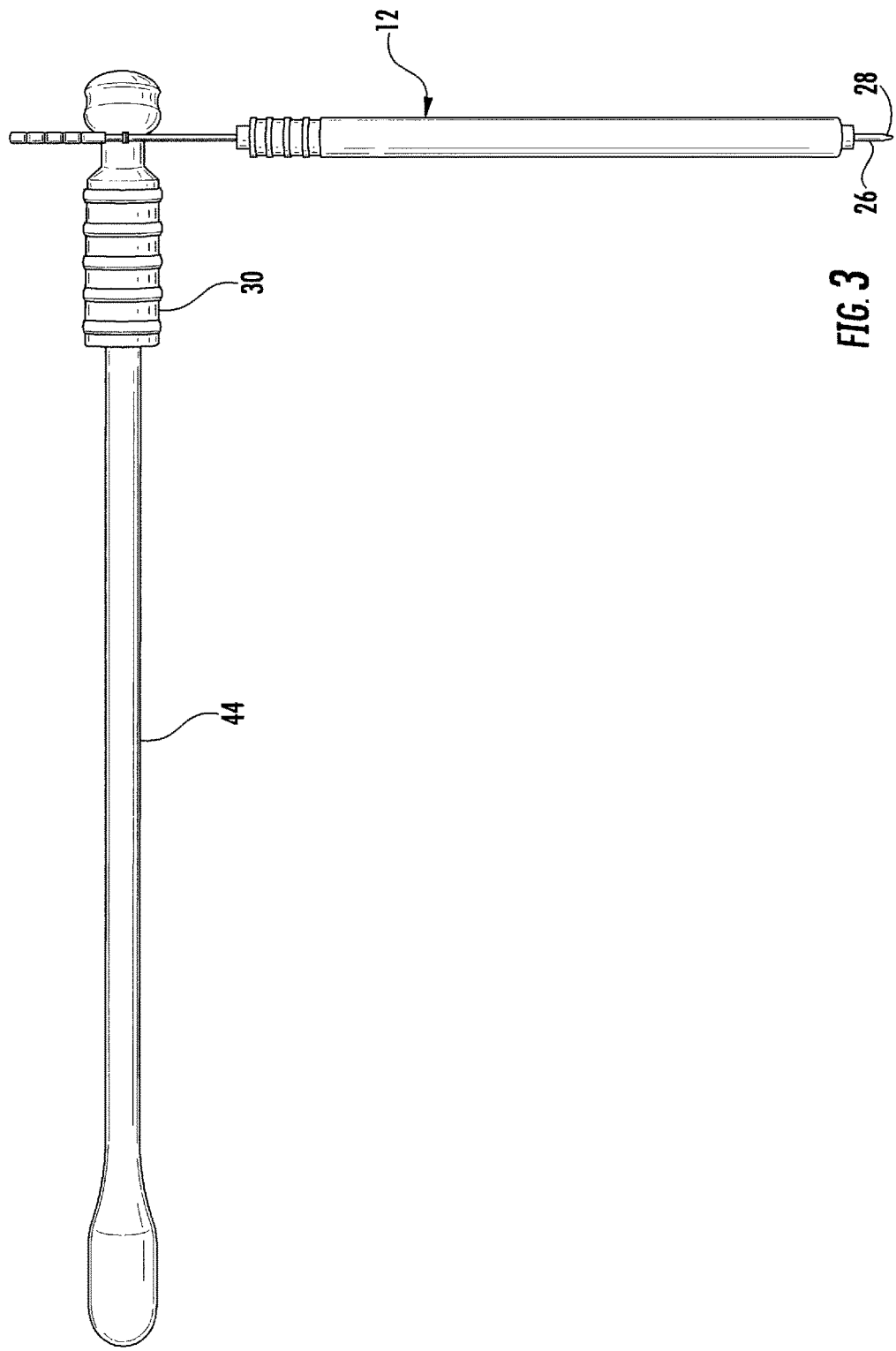
FIG. 3 is a plan view of one embodiment of the access assembly of the present invention, illustrated with a second stage dilator in place.
Figure 4:
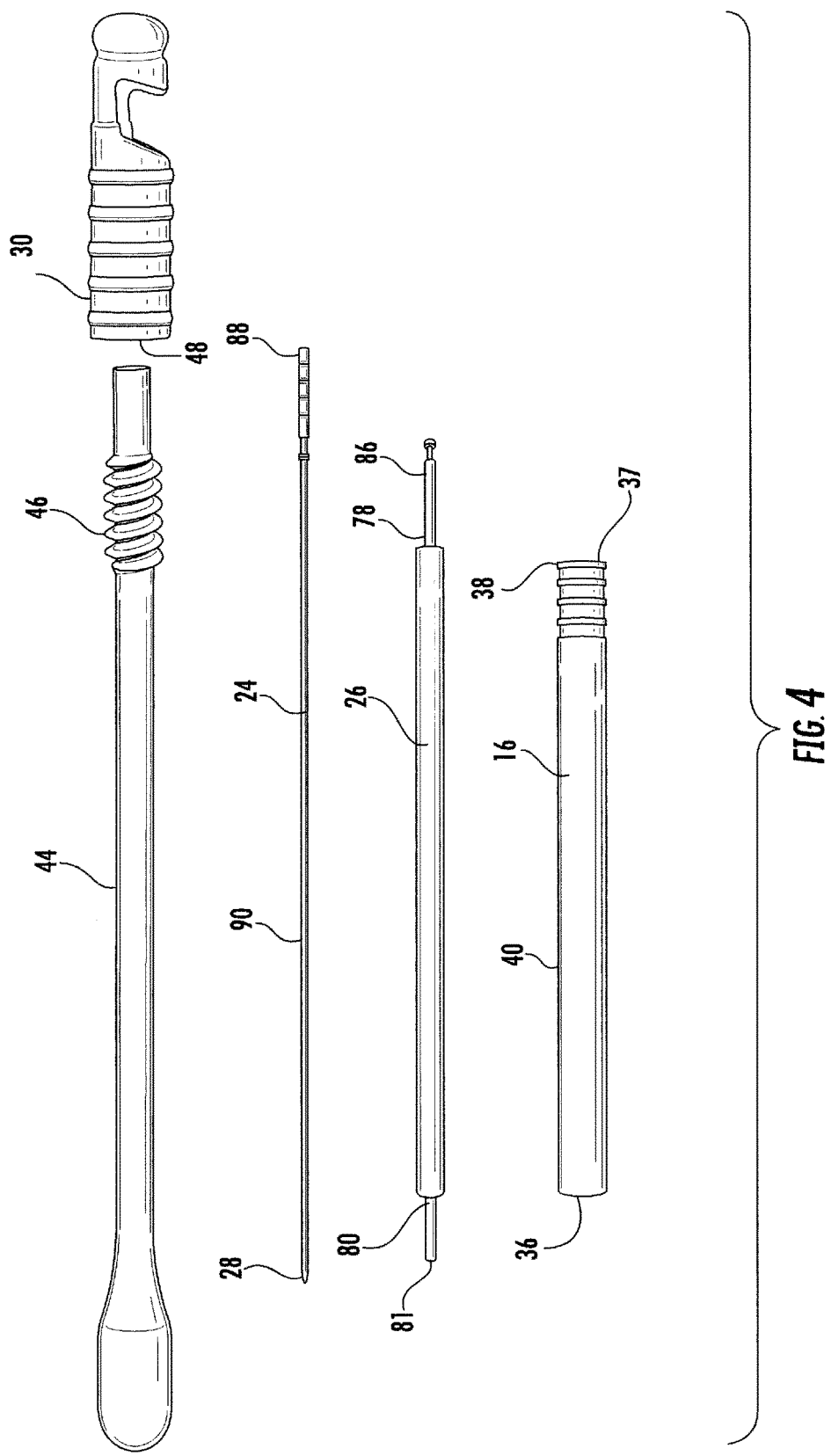
FIG. 4 is an exploded plan view of one embodiment of the access assembly of the present invention.
Figure 5:
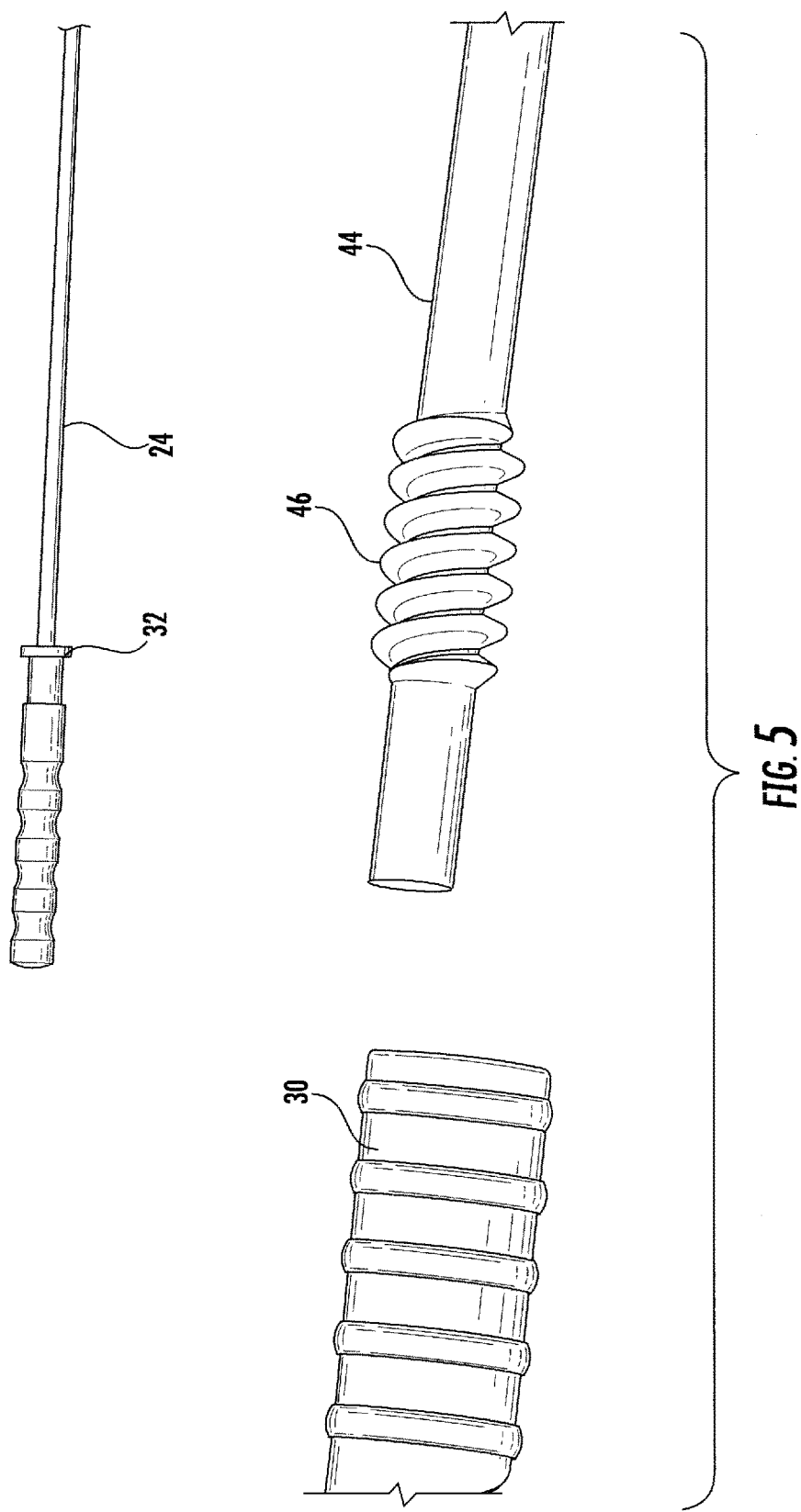
FIG. 5 is a partial exploded plan view illustrating the first end of the handle member and the second end of the needle member of the access assembly.
Figure 6:
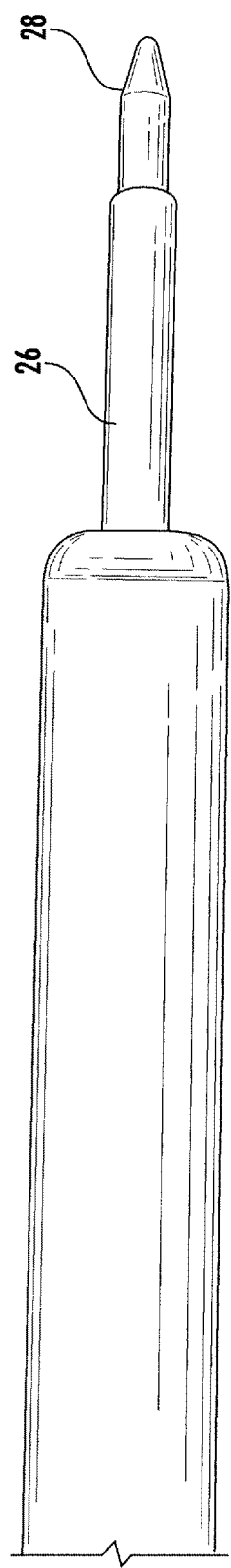
FIG. 6 is a partial view of the first end of one embodiment of the access assembly of the present invention.
Figure 7:
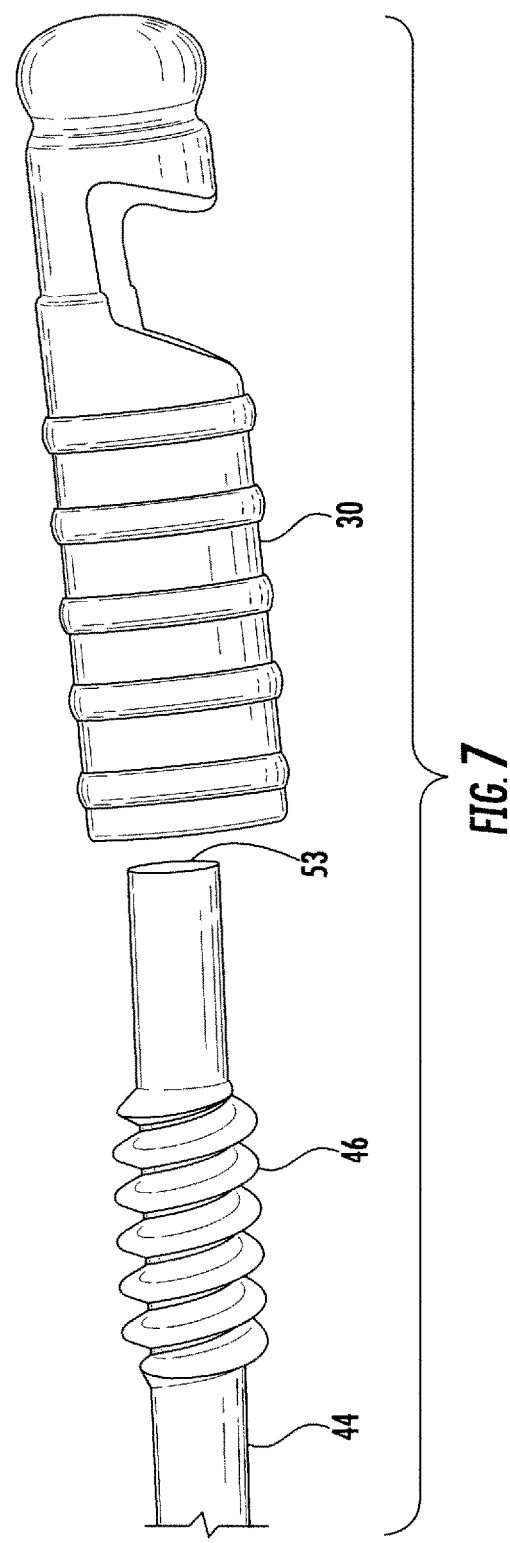
FIG. 7 is a partial orthographic view of the first end of the handle assembly.
Figure 8:
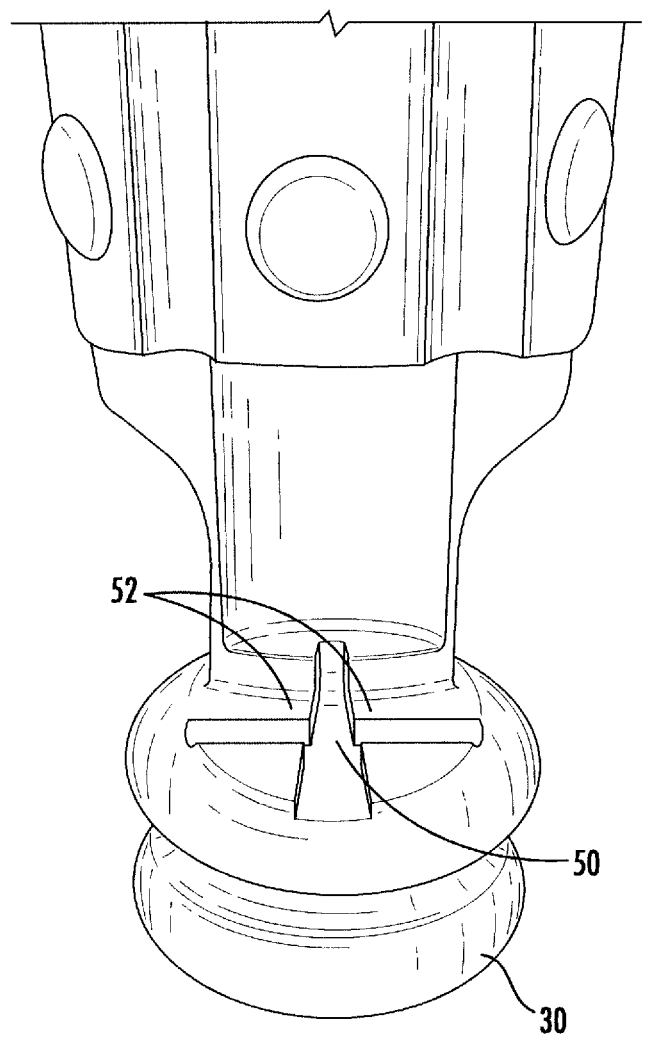
FIG. 8 is a partial orthographic view of the first end of the handle assembly illustrating the locking groove positioned in the unlocked position.
Figure 9:
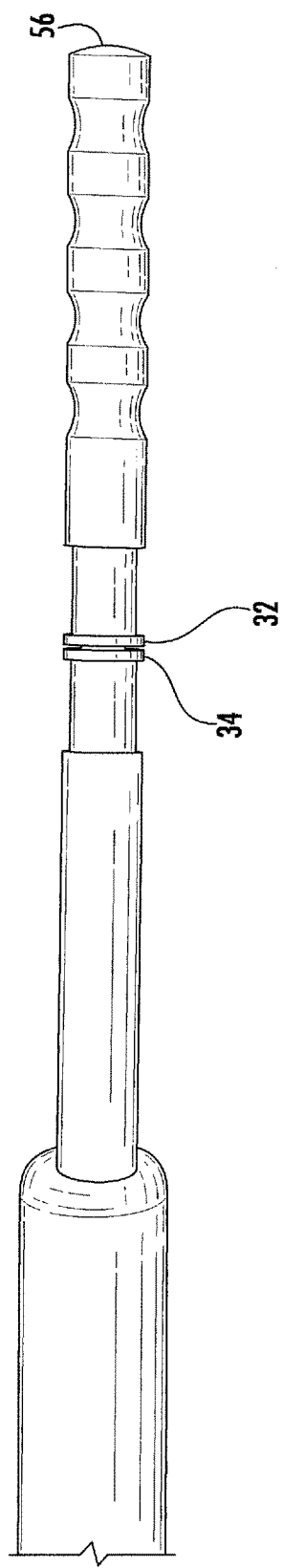
FIG. 9 is a partial orthographic view of the needle assembly illustrating the locking assembly without the handle assembly.
Figure 10:
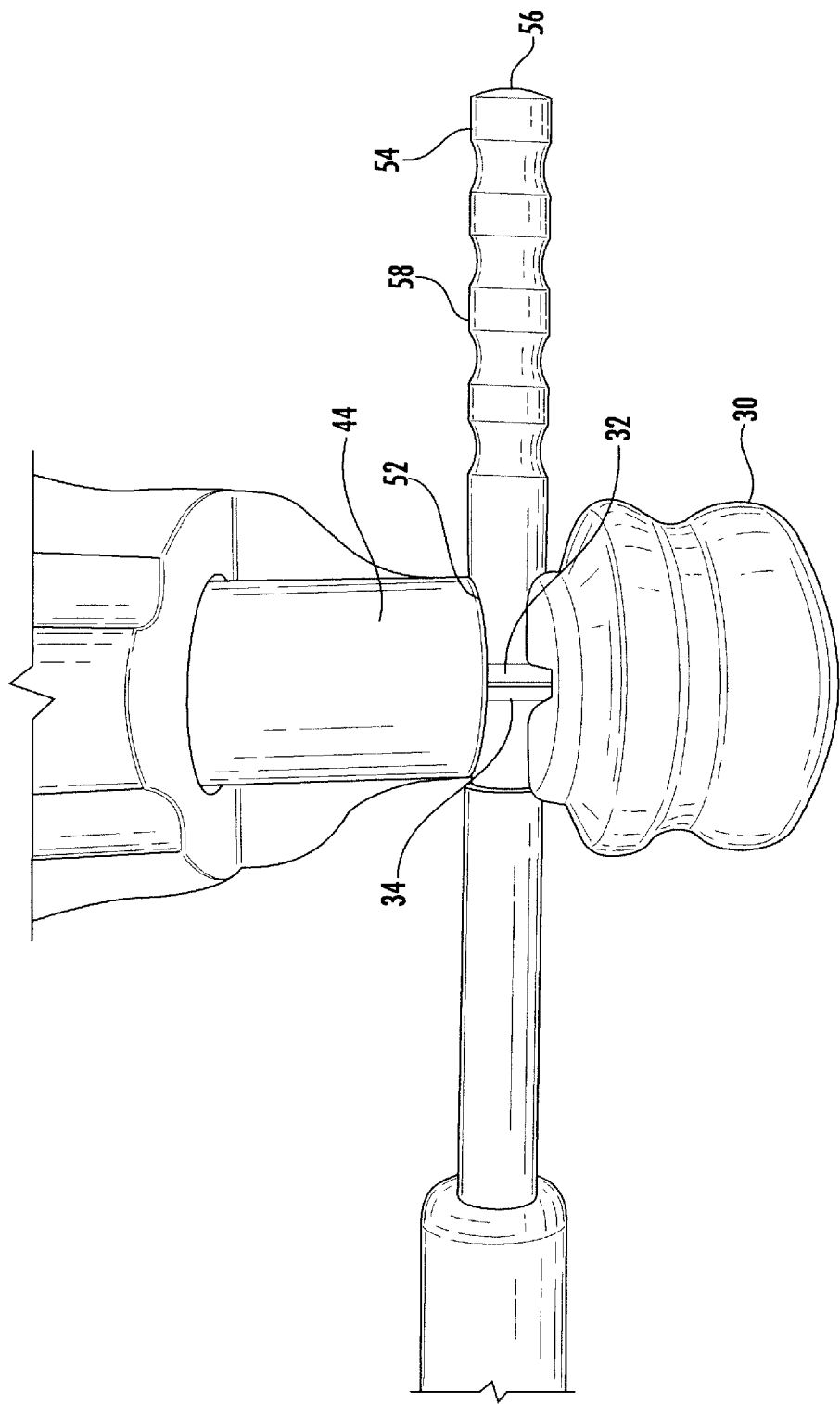
FIG. 10 is a partial perspective view of the first end of the handle assembly illustrated attaching the needle assembly together.

Referring generally to FIGS. 1-10, an access assembly constructed and arranged for anterior, lateral or anterolateral spinal procedures is illustrated. The present invention provides for the entire surgical procedure to be performed through a relatively small perforation or incision, and may be performed in either the thoracic or lumbar spine. In the preferred embodiment, the access assembly (10) comprises a needle assembly (12), a handle assembly (14), and at least one dilator tube (16). Some embodiments additionally include a guide wire (18). The needle assembly (12) is provided for initial insertion into the disc space through a small incision in the patient with the assistance of x-rays, thorascope, image intensifier, direct vision or the like. For example, for surgery in the thoracic spine, a small incision or perforation is made in the chest cavity of the patient from a lateral approach to the thoracic spine. For surgery in the lumbar spine, a small incision or perforation may be made in the abdominal wall of the patient. The first end (22) of the needle assembly (12) may be inserted with the assistance of the handle assembly (14), which connects the needle member (24) within the lumen (81) of the cannula (26), having the point (28) of the needle member (24) extending beyond the end point of the first end (84) of the cannula (26), and provides directional control of the needle assembly (12). In the preferred embodiment, the handle assembly (14) is oriented at a right angle with respect to the needle assembly to provide the surgeon with an angular reference to the trajectory of the needle assembly (12). The needle member (24) includes a point end (28), a central portion (90), and a second end (88). An outer diameter of the central portion being sized to fit snugly through the lumen (81) of the cannula (26). The point (28) of the needle member (24) may include a particular shape that aids in the insertion such as, but not limited to, a conical point, trocar, spherical or blunt. Once positioned, the needle assembly (12) extends between the disc space to outside of the patient to provide a guideway for the guide wire (18), as well as the dilator tube(s). In operation, the needle member (24) is separated from the cannula (26) by rotating a clamp portion (30) of the handle assembly (14) to release the first clamp ring (32) of the needle member from the second clamp ring (34) at the second end (86) of the cannula. The needle may then be removed from the cannula, leaving a tunnel to the disc space. A guide wire (18) or the like may then be placed through the cannula (26) into the disc space. The guide wire (18) includes a first end (63), a second end (64) and a center portion (66). The first end (63) is preferably spherical in shape, but may be tapered, pointed, blunt, trocar or any other desirable shape. The second end of the guide wire (18) generally includes a blunt square cut. The guide wire (18) is preferably constructed from a biocompatible metal material, such as spring tempered stainless steel or nitinol. However, it should be noted that any material having sufficient rigidity to act as a guideway for the tools, implants and the like may be utilized without departing from the scope of the invention. Dilator tube(s) may be placed over the outer diameter of the cannula (26) either before insertion or after. Thereafter, removal of the cannula (26), along with inner dilator tubes, provides an access tunnel to the disc space, while the guide wire (18) provides a guide surface to the disc space for transfer of tools, implants and the like. The tunnel is provided with sufficient diameter for disc modification or removal as well as the placement of spacers, bone fragments, implants and the like to be passed therethrough to the disc space.

The first dilator tube (68) is generally an elongated tubular member having a first end (70), a central portion (74) and a second end (72). Extending through the central portion (74) of the dilator tube is a central aperture (76) sized for cooperation with the outer surface (78) of the center portion (80) of the cannula (26). The second dilator tube (16) is generally an elongated tubular member having a first end (36), a central portion (40) and a second end (38). Extending through a central portion of the dilator tube(s) is a central aperture (37) sized for cooperation with the outer surface of the central portion (74) of the first dilator tube (68). Any number of successive dilator tubes may be provided without departing from the scope of the invention. The first end (36), (70) of the dilator tubes (16), (68) preferably includes a tapered or rounded first end (36), (70) for ease of insertion into the tissue leading to the disc space. In a most preferred embodiment, the tapered first end (36), (70) includes a rounded shape. However, it should be noted that other shapes may be utilized for the rounded end so long as they provide a smooth transition from the outer diameter of the guide wire cannula to the outer diameter of the dilator. Such shapes may include, but should not be limited to spherical, bullet, pyramid or suitable combinations thereof. The first dilator tube (68) is preferably secured directly about the outer surface of the cannula (26), while each successive dilator tube is constructed and arranged to fit snugly about the outer diameter of the prior dilator tube. The outer surface (60) of each respective dilator tube (16) is preferably round to act as a guide surface for the next successive dilator tube. However, it should be noted that other matched shapes may be utilized without departing from the scope of the invention. Such matched shapes may include, but should not be limited to ovals, polygons and the like. It should also be noted that in at least one embodiment, the components of the system are constructed to either be constructed from electrically conductive materials or include electrically conductive pathways for use with neurophysiological monitoring equipment (82) as is known in the art.

Referring to FIGS. 2, 8-10, assembly of the needle and cannula to the handle assembly is illustrated. The handle assembly (14) includes a clamp portion (30) and a rod portion (44). In the preferred embodiment, the rod portion is provided with male threads (46) while the clamp portion is provided with female threads (48) (FIG. 4) which interact to allow the clamp portion to be moved along the end portion of the rod member. However, it should be noted the male and female threads could be reversed without departing from the scope of the invention. It should also be noted that mechanical or electrical means could be provided to provide a clamping force to the needle assembly without departing from the scope of the invention. The clamp portion (30) includes a groove (50) having a pair of generally flat opposing side surfaces (52) spaced a predetermined distance apart and extending along the length of the groove (50). The end of the rod portion likewise includes an indention (53). The groove and the indention cooperate with the first and second clamping rings (32), (34) to secure the needle member (24) within the cannula (26) by using the threads to force the distal end of the rod against the groove of the clamp portion. The second end (54) of the needle member (24) is provided with an anvil surface (56) suitable for striking with a mallet or the like. A gripping surface (58) is also provided for grasping and/or rotation of the needle member.

All patents and publications mentioned in this specification are indicative of the levels of those skilled in the art to which the invention pertains. All patents and publications are herein incorporated by reference to the same extent as if each publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification.

One skilled in the art will readily appreciate that the present invention is well adapted to carry out the objectives and obtain the ends and advantages mentioned, as well those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An access assembly (10) for anterior, lateral and anterolateral spinal procedures comprising:
    a needle assembly (12), including a cannula (26) and a needle member (24), said cannula (26) formed as a tubular member having a first end (84), a second end (86) and a central portion (80), a lumen (81) extending through said cannula (26), said needle member (24) having a point end (28), a second end (88) and a central portion (90) having an outer diameter sized to fit through said lumen (81), said second end (86) of said cannula (26) includes a first clamp ring (32), said second end (88) of said needle assembly (24) includes a second clamp ring (34), said first clamp ring (32) and said second clamp ring (34) constructed and arranged to be positioned adjacent with respect to each other and cooperating with a clamp portion (30) of a handle assembly (14);
    a handle assembly (14) for providing directional control of said needle assembly (12) during insertion thereof, said handle assembly (14) being removable and resecurable to said needle assembly (12), said handle assembly (14) includes a clamp portion (30) cooperating with said adjacently positioned first clamp ring (32) and said second clamp ring (34) for securing said handle assembly (14) to said needle assembly (12), said clamp portion (30) simultaneously securing said needle member (24) within said lumen (81) of said cannula (26) having said point (28) of said needle member (24) extending beyond an end point of said second end (86) of said cannula (26).

2. The access assembly (10) for anterior, lateral and anterolateral spinal procedures of claim 1 wherein said clamp portion (30) includes a groove (50) having a pair of generally flat opposing side surfaces (52) spaced a predetermined distance apart and extending along the length of the groove (50), said groove sized to span said first and said second clamp rings (32), (34) respectively.

3. The access assembly (10) for anterior, lateral and anterolateral spinal procedures of claim 2 wherein said clamp portion (30) of said handle assembly (14) includes a rod portion (44) which cooperates with said clamp portion (30) to secure said first and said second clamp rings (32), (34) within said clamp portion, a threaded engagement provides controlled movement between said rod portion (44) and clamp portion (30) by using said threads to force the distal end of said rod portion (44) against the groove (50) of said clamp portion (30).

4. The access assembly (10) for anterior, lateral and anterolateral spinal procedures of claim 2 wherein said second end (88) of said needle member (24) includes an anvil surface (56) suitable for striking with a mallet.

5. The access assembly (10) for anterior, lateral and anterolateral spinal procedures of claim 1 including a first dilator tube (68), said first dilator tube (68) is generally an elongated tubular member having a first end (70), a central portion (74) and a second end (72) having a central aperture (76) sized for cooperation with the outer surface (78) of the center portion (80) of the cannula (26) extending through a central portion thereof.

6. The access assembly (10) for anterior, lateral and anterolateral spinal procedures of claim 5 including a second dilator tube (16), said second dilator tube (16) is generally an elongated tubular member having a first end (36), a central portion (40) and a second end (38) having a central aperture (37) sized for cooperation with the outer surface of the central portion (74) of the first dilator tube (68) extending through a central portion (40) of said second dilator tube (16).

7. The access assembly (10) for anterior, lateral and anterolateral spinal procedures of claim 1, including a guide wire (18), said guide wire (18) including a first end (63), a second end (64) and a center portion (66), said center portion (66) sized to fit through said lumen (81) of said cannula (26).

8. The access assembly (10) for anterior, lateral and anterolateral spinal procedures of claim 1, wherein said handle assembly (14) is oriented at a right angle with respect to said needle assembly (12) to provide the surgeon with an angular reference to the trajectory of said needle assembly (12).

9. The access assembly (10) for anterior, lateral and anterolateral spinal procedures of claim 1, wherein said needle member (24) is constructed from electrically conductive materials for use with neurophysiological monitoring equipment (82).

10. The access assembly (10) for anterior, lateral and anterolateral spinal procedures of claim 1, wherein said needle member (24) includes electrically conductive pathways for use with neurophysiological monitoring equipment (82).

11. The access assembly (10) for anterior, lateral and anterolateral spinal procedures of claim 1, wherein said cannula (26) is constructed from electrically conductive materials for use with neurophysiological monitoring equipment (82).

12. The access assembly (10) for anterior, lateral and anterolateral spinal procedures of claim 1, wherein said cannula (26) includes electrically conductive pathways for use with neurophysiological monitoring equipment (82).

* * * * *